United States Patent
Braam et al.

(10) Patent No.: US 8,721,527 B2
(45) Date of Patent: May 13, 2014

(54) ENDOSCOPIC DISSECTOR

(75) Inventors: Marjorie J. I. Braam, Den Haag (NL); Markus J. C. Smeulders, Amsterdam (NL); John K. Stanley, Lancashire (GB); David Cottier, Chester (GB)

(73) Assignee: Medical Device Innovations Ltd., Halton (GB)

( * ) Notice: Subject to any disclaimer, the term of this patent is extended or adjusted under 35 U.S.C. 154(b) by 1306 days.

(21) Appl. No.: 11/815,970

(22) PCT Filed: Feb. 10, 2006

(86) PCT No.: PCT/GB2006/000469
§ 371 (c)(1),
(2), (4) Date: Feb. 7, 2008

(87) PCT Pub. No.: WO2006/085090
PCT Pub. Date: Aug. 17, 2006

(65) Prior Publication Data
US 2008/0255600 A1    Oct. 16, 2008

(30) Foreign Application Priority Data

Feb. 10, 2005 (GB) .................................. 0502772.7

(51) Int. Cl.
*A61B 1/00* (2006.01)
*A61B 1/04* (2006.01)

(52) U.S. Cl.
USPC ............................. 600/127; 600/114; 600/129

(58) Field of Classification Search
USPC .................. 600/114, 127, 128, 121–125, 175
See application file for complete search history.

(56) References Cited

U.S. PATENT DOCUMENTS

| 4,807,593 | A | * | 2/1989 | Ito ................................. 600/114 |
| 5,667,480 | A |   | 9/1997 | Knight et al. ................ 600/210 |
| 5,938,680 | A | * | 8/1999 | Ginn ............................. 606/190 |
| 6,019,771 | A |   | 2/2000 | Bennett et al. |
| 6,042,538 | A |   | 3/2000 | Puskas |
| 6,387,043 | B1 | * | 5/2002 | Yoon ............................. 600/109 |
| 6,520,908 | B1 | * | 2/2003 | Ikeda et al. .................... 600/132 |

(Continued)

FOREIGN PATENT DOCUMENTS

| BE | 1006811 | 12/1994 |
| EP | 0 769 270 | 4/1997 |

(Continued)

OTHER PUBLICATIONS

International Preliminary Report on Patentability for International Application No. PCT/GB2006/000469 dated May 16, 2007.

(Continued)

*Primary Examiner* — Alireza Nia
(74) *Attorney, Agent, or Firm* — Marshall, Gerstein & Borun LLP

(57) ABSTRACT

A dissection device comprising an elongate cannula having proximal and distal ends and a central axis and arranged to receive at least a remote viewing device therein, a handle arranged to be attached to the proximal end of the elongate cannula and a dissection tip arranged to be attached to the distal end of the elongate cannula, the dissection tip comprising a curved hollow shroud that when the dissection tip is orientated for use defines a substantially concave working cavity having an open underside, the hollow shroud comprising a pair of laterally extending lateral extensions, each wing extending from an opposing lateral portion of the periphery of the hollow shroud.

24 Claims, 12 Drawing Sheets

(56) References Cited

U.S. PATENT DOCUMENTS

| | | | |
|---|---|---|---|
| 6,592,582 B2* | 7/2003 | Hess et al. | 606/49 |
| 6,596,010 B1 | 7/2003 | Herman et al. | 606/192 |
| 7,314,479 B2* | 1/2008 | Wellman et al. | 606/205 |
| 7,431,694 B2* | 10/2008 | Stefanchik et al. | 600/104 |
| 2003/0065323 A1 | 4/2003 | Hess et al. | 606/49 |
| 2003/0195544 A1 | 10/2003 | Hess et al. | 606/190 |
| 2003/0195545 A1 | 10/2003 | Hermann et al. | 606/191 |

FOREIGN PATENT DOCUMENTS

| | | | |
|---|---|---|---|
| JP | 09-000528 | 1/1997 | |
| JP | 9-122133 | 5/1997 | |
| JP | 10-504472 | 5/1998 | |
| WO | WO-95/31926 | 11/1995 | |
| WO | WO 99/12477 | 3/1999 | A61B 17/00 |
| WO | WO 99/39632 | 8/1999 | A61B 5/00 |
| WO | WO 00/71033 | 11/2000 | A61B 17/00 |

OTHER PUBLICATIONS

International Search Report for-International Application No. PCT/GB2006/000469 dated Apr. 18, 2006.

Written Opinion of International Searching Authority for International Patent Application No. PCT/GB2006/000469.

Search Report Under Section 17 for GB0602759.3 dated Jul. 18, 2006.

Examination Report in CA Application No. 2,597,479 dated Apr. 20, 2011, 3 pages.

Examination Report in EP Application No. 06 709 707.1 dated Oct. 8, 2010, 6 pages.

Translation of The First Office Action in CN Application No. 200680008422.7 dated Feb. 6, 2009, 6 pages.

Translation of the Notice on The Second Office Action in CN Application No. 200680008422.7 dated Oct. 18, 2011, 5 pages.

Translation of Notice of Reasons for Rejection in JP Application No. P2007-554642 dated Aug. 31, 2010, 3 pages.

* cited by examiner

ENDOSCOPIC DISSECTOR

The present invention relates to a method and apparatus for minimally invasive surgery.

Traditional surgical treatment of various conditions typically involves making an incision in the relevant area of a patient's body to provide direct access and vision to the relevant internal structure, be that an internal organ, other muscular or vascular structures or bone. The incision tends to be relatively large so as to allow the required direct vision and direct access and typically dissects a number of tissue and muscle layers. Disadvantages of these traditional surgical techniques include the build up of scar tissue at the incision and may cause further complications or detrimental physical effects on the patient and the unsightly visible scaring on the patient's skin that usually results. Minimally invasive surgery seeks to overcome these disadvantages by introducing remotely operated surgical instruments into cavities within the patient's body via relatively small incisions on the patient's skin. Such procedures are typically done using fibre optic endoscopes. Endoscopy is the examination and inspection of the interior of body organs, joints or cavities through an endoscope. An endoscope is a device using fibre optics and power lens systems to provide lighting and visualisation of the interior of a body section. The portion of the endoscope inserted into the body may be rigid or flexible, depending upon the medical procedure.

In addition to being used to diagnose various conditions, endoscopy can also guide therapy and repair, such as the removal of torn cartilage from the weight bearing and articulation surfaces of a joint. Biopsy (tissue sampling for pathologic testing) may be also performed under endoscopic guidance. Local or general anaesthetic may be used during endoscopy, depending upon the type of procedure being formed. The incision needed for the insertion of an endoscope is much smaller than would be the case for performing the same procedure without the aid of this instrument.

When performing endoscopic surgery a working cavity usually exists either naturally or artificially, having been created as part of the procedure e.g. gas insufflation of the abdominal cavity. Examples of working cavities are the abdomen in laparoscopy and the uterus in gynaecology. Even within orthopaedic surgery, where surgery of joints is performed, there are already such cavities, although they may be relatively small. However, there are no such cavities in the body's extremities, such as the hands and feet. To create working cavities within such extremities it is therefore necessary to perform dissection between two anatomical layers.

An example of a device for performing such dissection is shown in U.S. Pat. No. 6,596,010 B1. The dissection device shown in this document includes a pushing member, such as a support tube, for creating a tunnel alongside an elongate vessel in the body, such as a vein. In use, the pushing member, which may have a blunted dissection tip, is pushed along a vein or blood vessel to separate it from the surrounding tissue. An endoscope may be introduced through the support tube to allow remote viewing of the area under dissection. However, the device shown in U.S. Pat. No. 6,596,010 is designed specifically for harvesting veins or blood vessels for use in coronary bypass surgery and is not suited for other minimally invasive surgery techniques. For example, there is no facility to allow the insertion of suitable microsurgery instruments through the support tube and the shape of the dissector tip does not provide good viewing during dissection.

International patent application WO 99/39632 discloses a device for minimally invasive surgery, and particularly the harvesting of veins, that includes a shaft having a handle mounted on one end and a dissecting tip on the other end. The dissecting tip optionally includes a light source such that the vein is transilluminated through the patient's skin. This allows the vein to be viewed exterior of the patient and the device to be guided exterior to the patient by means of the transillumination. The dissecting tip is a concave spoon shape orientated to reflect the illumination through the patient's skin.

Belgium patent application BE09300315 discloses a dissector device consisting of a metal rod with a flattened and rounded tip at its distal end. The instrument can include a spoon-shaped section that may define a small working cavity. The rod is solid in cross section.

Embodiments of the present invention therefore seek to provide a dissection device for minimally invasive surgery and a method of use of such a device that substantially mitigate against the disadvantages of known dissecting instruments.

According to a first aspect of the present invention there is provided a tissue dissection tip arranged to be attached to the distal end of an elongate cannula, the dissection tip comprising a curved hollow shroud that when the dissection tip is orientated for use defines a substantially concave working cavity having an open underside, the hollow shroud comprising a pair of laterally extending lateral extensions, each lateral extension extending from an opposing lateral portion of the periphery of the hollow shroud, wherein through a cross-section perpendicular to the central axis of the cannula the hollow shroud has an outer surface having a substantially convex portion and each lateral extension has a substantially concave outer surface whereby the substantially outer concave surface of each lateral extension lifts the upper dissected tissue.

Additionally or alternatively, the dissection tip may comprise a tissue dissection portion located at the distal end of the dissection tip, the tissue dissection portion terminating in a plane that, when the dissection device is orientated for use, is above a plane in which the remote viewing device is arranged to lie in within the cannula. Preferably, when viewed through an axial cross-section, the tissue dissection portion has a substantially concave outer surface that is contiguous with the convex outer surface of the hollow shroud.

According to a second aspect of the present invention there is provided a dissection device comprising an elongate cannula having proximal and distal ends and a central axis, a handle arranged to be attached to the proximal end of the elongate cannula and a tissue dissection tip according to the first aspect of the present invention. The cannula may be further arranged to receive at least one surgical instrument therein. Equally, the cannula may additionally or alternatively include an elongate slot arranged to engage a surgical instrument and guide said instrument along said slot.

The handle may comprise a viewing device holding mechanism, said viewing device holding mechanism being arranged to translate a viewing device within the cannula between a first and second position. Preferably, in the first position the distal end of a remote viewing device held by the viewing device holding mechanism extends beyond the distal end of the cannula and into the working cavity defined by the curved hollow shroud.

Additionally or alternatively, the viewing device holding mechanism may comprise an actuating lever arranged to be operated by a user whilst gripping the handle.

The body portion of the handle may be arranged to house a fibre optic cable for connection to the remote viewing device. Furthermore, the handle may also comprise a fibre optic cable retention mechanism arranged to secure a fibre optic cable within the handle. The fibre optic cable retention mechanism may comprise a pair of resilient seals defining a slot arranged to receive the fibre optic cable there-through.

Additionally or alternatively, the body portion may include a longitudinal groove in communication with the interior of the cannula. The longitudinal groove is preferably tapered in width towards the cannula.

The handle may further comprise a grip portion arranged to provide a gripping area for a user's hand, the grip portion extending in a direction lateral to the axis of the cannula.

The cannula may additionally or alternatively comprise a plurality of internal longitudinal passageways. At least two of the internal longitudinal passageways may be in communication with one another.

According to a further aspect of the present invention there is provided a method for performing minimally invasive surgery, the method comprising the steps of making an incision in a body, which incision provides access to a natural tissue plane, introducing a dissector device in accordance with the previous aspect of the present invention into the incision, dissecting first and second tissue layers from one another along the tissue plane by exerting a lateral force on the dissector device so as to advance the dissector device along the tissue plane and performing a surgical procedure within the anatomical space created by the dissector device.

The method preferably includes providing an endoscope in the dissector device in a first position wherein the endoscope provides a direct view of the area of tissue being dissected and subsequently withdrawing the endoscope to a second position prior to commencement of the surgical procedure wherein the endoscope provides a direct view of the anatomical space.

The above method is preferably provided for the treatment of any one or more of the following: DeQuervain's disease, compartment syndrome, vein harvesting, tendon harvesting, tendon transfer, muscle transfer, Carpel Tunnel syndrome or plastic surgery.

Embodiments of the present invention will now be described, by way of illustrative example only, with reference to the accompanying figures, of which:

FIG. 1 schematically illustrates the external tissue layers of the human body;

Figure 7:
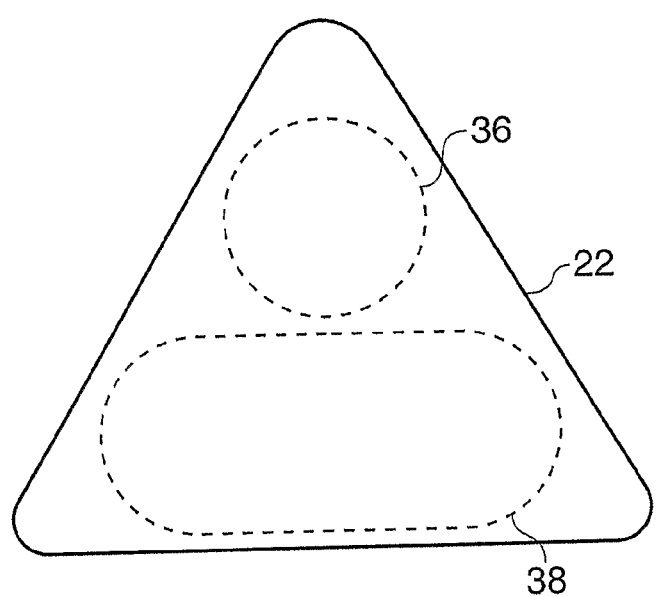
Figure 8:
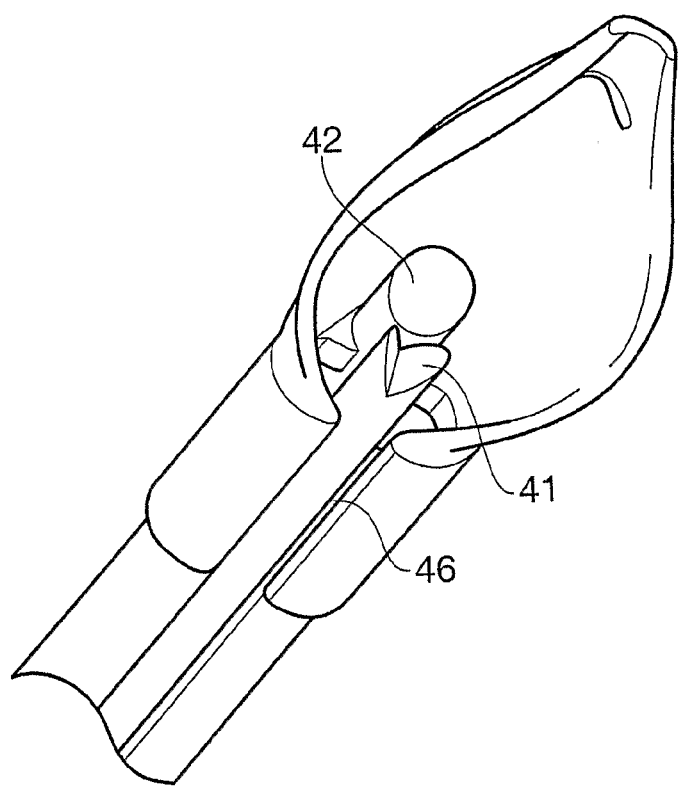
Figure 9:
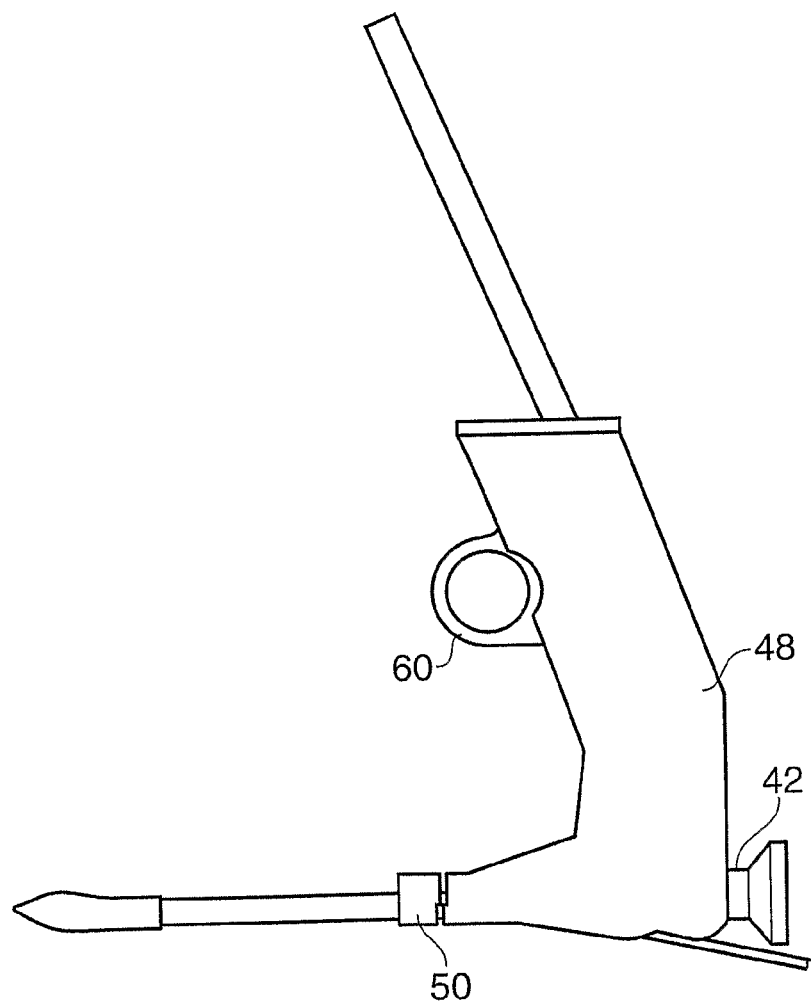
Figure 10:
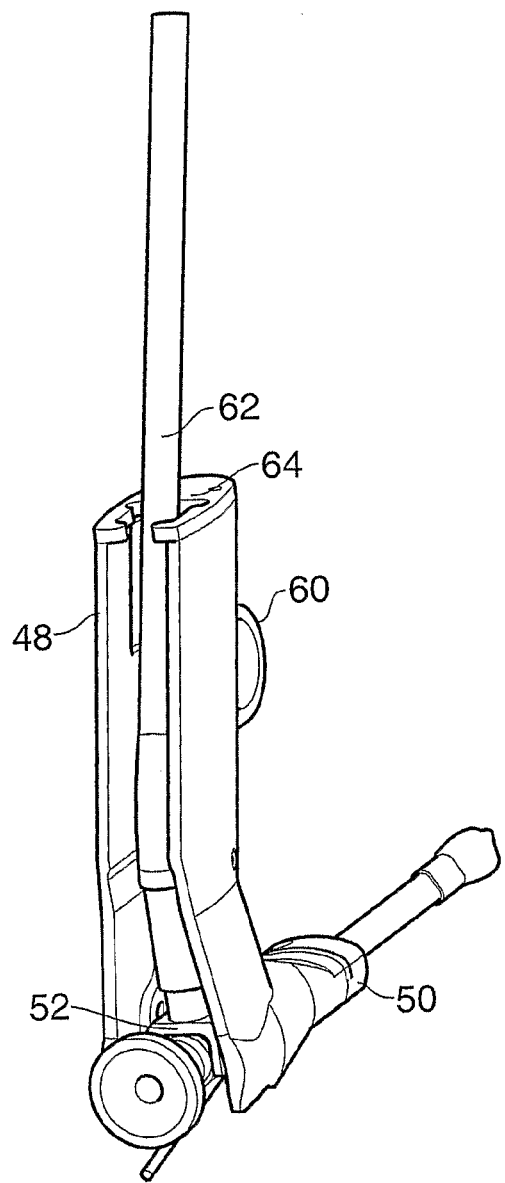
Figure 11:
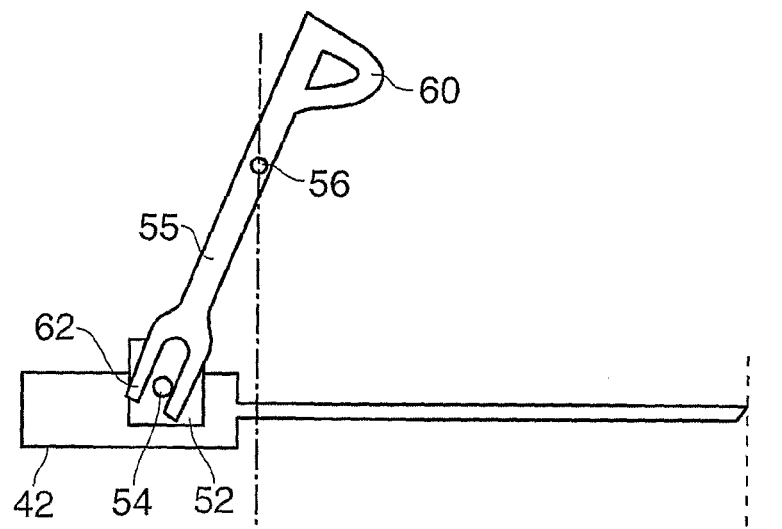
Figure 12:
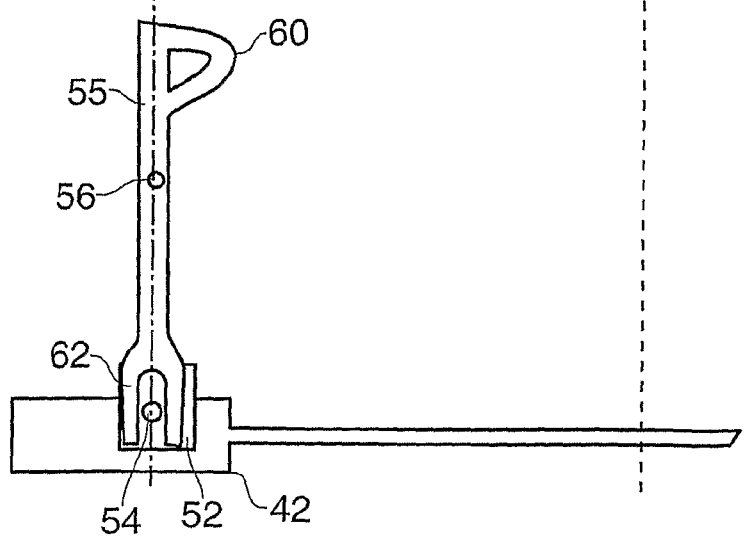
Figure 13:
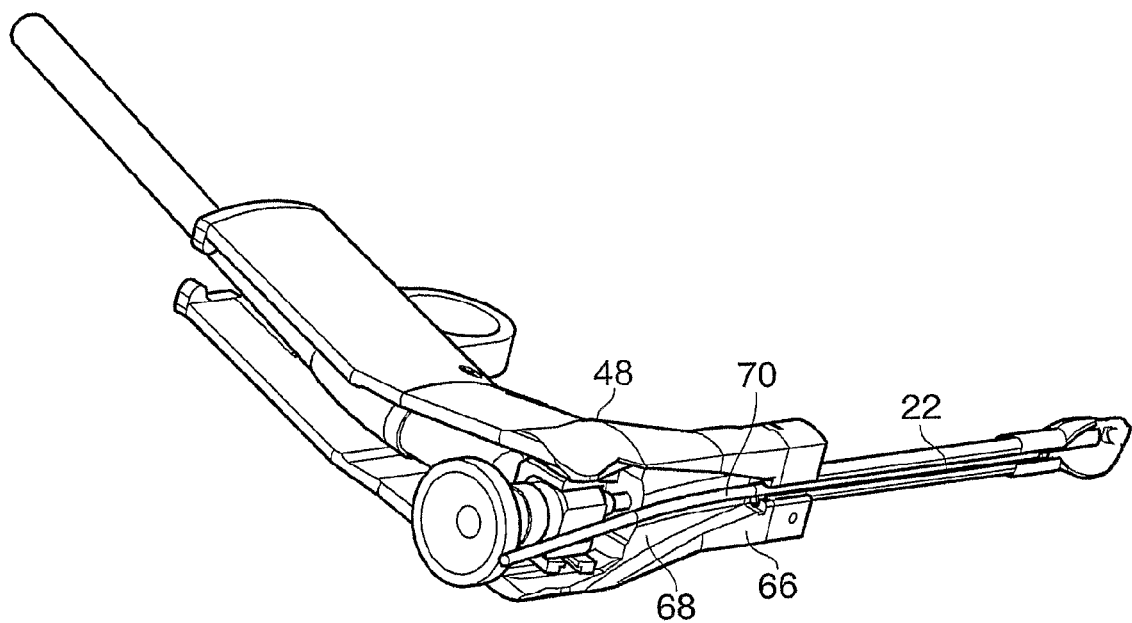

FIG. 7 schematically illustrates the cross-sectional view of the cannula in accordance with an embodiment of the present invention;

FIG. 8 illustrates a bottom perspective view of the dissector tip shown in FIGS. 2-5 with an endoscope in the retracted position;

FIG. 9 illustrates a side elevation of a dissector device according to an embodiment of the present invention;

FIG. 10 illustrates a rear perspective view of the dissector device shown in FIG. 9;

FIG. 11 schematically illustrates the endoscope movement mechanism of an embodiment of the present invention with the endoscope in the retracted position;

FIG. 12 schematically illustrates the endoscope movement mechanism of an embodiment of the present invention with the endoscope in the extended position; and FIG. 13 illustrates a bottom perspective view of the dissector device shown in FIGS. 9 & 10.

Figure 1:
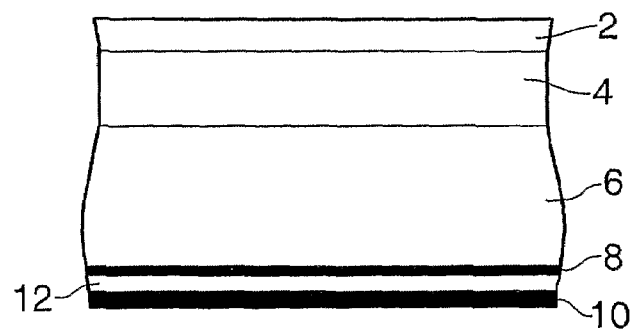

A schematic representation of the outer layers of human skin and tissue is shown in FIG. 1. The outer layer of tissue comprises the epidermis 2, of which the outer layer is the skin. Underneath the epidermis is a further, thicker, layer referred to as the dermis 4. Beneath the dermis 4 is a further, thicker layer, the subcutaneous layer 6. It is within the subcutaneous layer 6 that the outer arteries and veins can be found, together with hair roots and sweat glands. Beneath the subcutaneous layer 6 is a layer referred to as the superficial fascia 8 (the deepest layer of the skin and subcutaneous tissue). Beneath the superficial fascia 8 is a further layer, referred to as the deep fascia (compartment fascia) 10. A potential space exists between the superficial fascia 8 and the deep fascia 10, which is referred to as the fascial cleft 12. The various layers illustrated in FIG. 1 form part of a connective-tissue network, referred as the superficial fascial system, which extends from the sub-dermal plane to the underlying muscle layers. It consists primarily of one to several thin, horizontal membrane sheets separated by varying amounts of fat with interconnecting vertical or oblique dividing walls. The precise anatomy of the superficial fascial system varies with sex, body region and amount of body fat. The primary function of the superficial fascial system is to encase, support and shape the fat of the surrounding body portion and to hold the skin onto the underlying tissues.

To perform minimally invasive surgery in the extremities, a working cavity must be formed by dissection between individual tissue layers. For example, a cavity can be obtained by dissection between the superficial compartment of skin and subcutaneous tissue and the deep compartment of muscle. Additionally, intramuscular dissections can be done between layers of muscle that are often separated by a vascular plane. A third example of a cavity can be made between certain bones and their overlying muscles.

Figure 2:
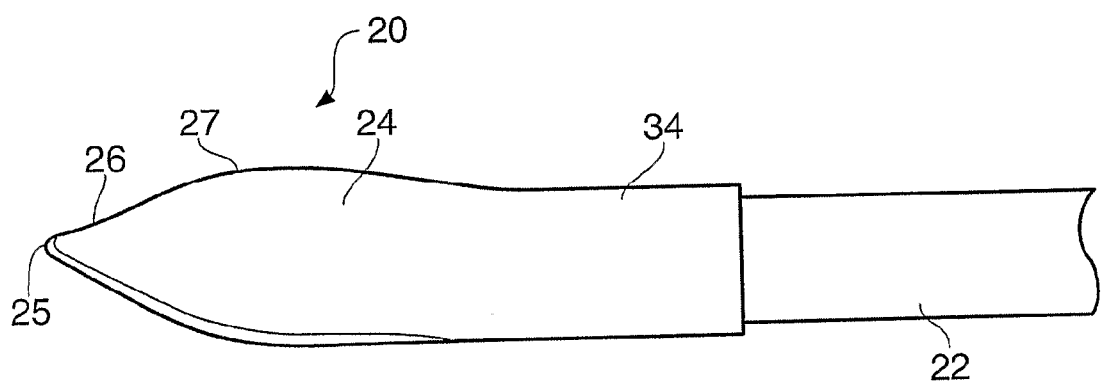
FIG. 2 illustrates a side elevation of a dissector tip according to an embodiment of the present invention.

The tip of a dissecting device according to an embodiment of the present invention and suitable for the dissection between layers of tissue and/or muscle is shown in FIGS. 2-5. The tip 20 is formed on, or connected to, the extremity of a hollow cannula 22 and comprises a main body 24 that forms a curved hollow shroud that is open on its underside. When viewed in side-profile, as shown in FIG. 2, the main body terminates at its distal end in a tissue dissection portion 25. As will be explained below, an endoscope or other direct viewing device extends through the cannula. To ensure that direct vision of the tissue structures ahead of the dissection portion 25 is possible, the dissection tip must be above the end of the endoscope or the viewing device, when viewed in the orientation shown in FIG. 2. This can also be seen from FIG. 6, which illustrates just the dissection tip 20 viewed head-on. The position in which an endoscope 42 would be is illustrated by the shaded circle. As can be seen, the tissue dissection portion 25 is arranged to be above the endoscope position. From the distal end of the main body the lower side-profile extends downwardly at an angle, preferably approximately 45°, until it is approximately level with, or slightly below, the lower extremity of the cannula 22, at which point the side-profile extends substantially parallel to the horizontal axis of the cannula to the proximal end of the tip 20. The upper side-profile extends upwardly from distal end of the main body, initially following a concave curve 26 that smoothly transitions to a convex curve 27 that continues to the proximal end of the tip 20. The presence of the double curvature in the upper side-profile provides improved tissue layer dissection, since the initial concave portion 26 lifts the upper tissue layer without creating a downward force on the dissection tip 20, which would be the case, if the upper side-profile was simply a continuous convex curve. The absence of a downwards force helps prevent the dissection instrument from digging into the lower tissue layer and damaging that tissue layer. In the preferred embodiment shown in the figures the side-profile of the dissection tip 20 creates neither a downward nor an upward force when in use.

Figure 3:
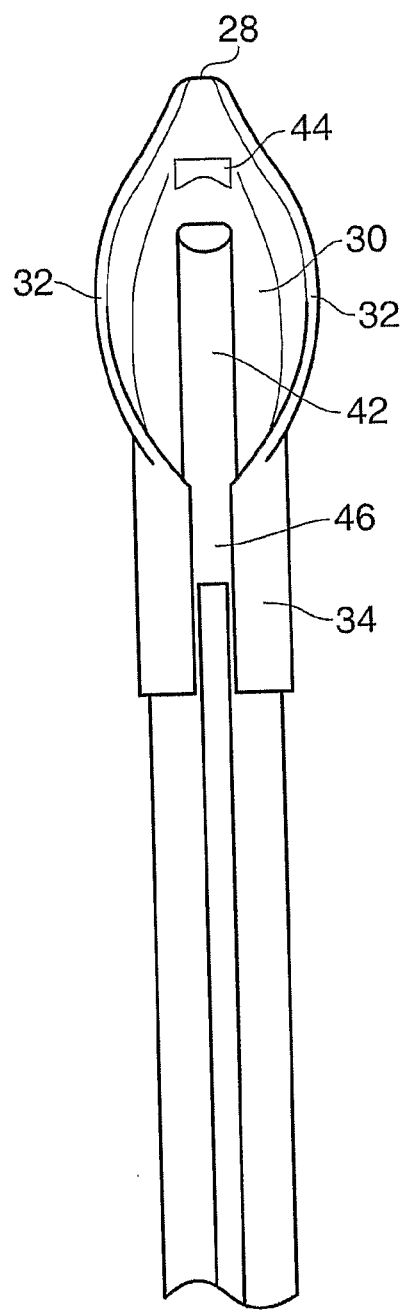
FIG. 3 illustrates the underside of the dissector tip shown in FIG. 2.
Figure 4:
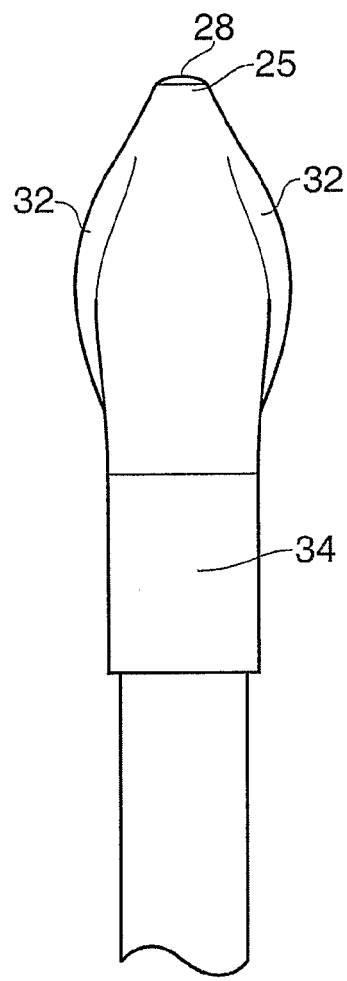
FIG. 4 illustrates a plan view of the dissector tip shown in FIGS. 2 & 3.

The tissue dissection portion 25 terminates the distal extremity of the dissection tip 20 with a blunt surface 28 orientated substantially perpendicular to the longitudinal axis of the tip 20 and the cannula 22, although in preferred embodiments, and as shown in FIGS. 3 and 4, the blunt surface is slightly curved. In use, the slightly curved blunt surface 28 acts as a wedge to force apart the desired tissue layers but is not pointed enough to cause the dissection portion 25 to dig into the tissue causing damage.

Figure 5:
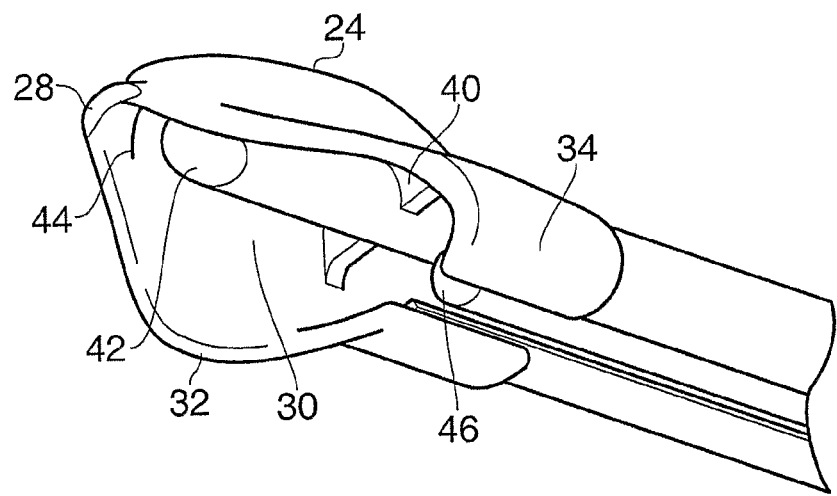
FIG. 5 illustrates a bottom perspective view the dissector tip shown in FIGS. 2-4 with an endoscope in the dissection mode of operation.
Figure 6:
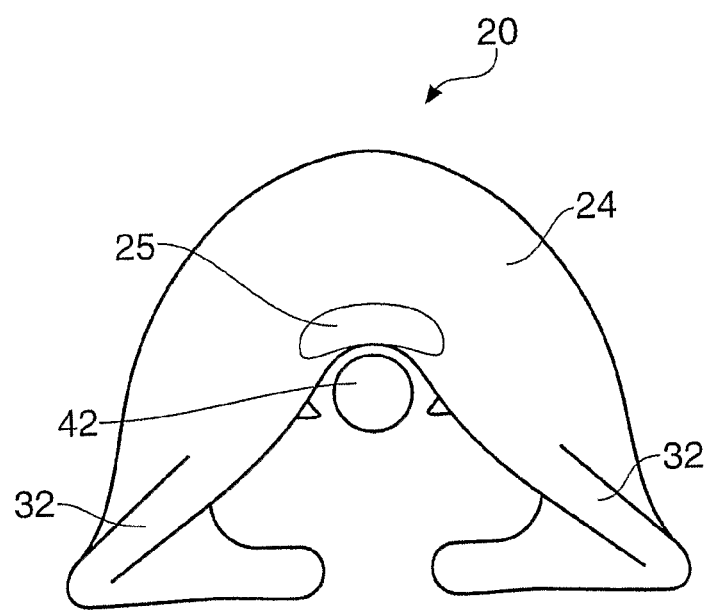
FIG. 6 illustrates a front elevation of the dissector tip shown in FIGS. 2-5.

As previously mentioned, and as best seen in FIGS. 3 and 5, the dissection tip 20 forms a hollow shroud that defines a working cavity 30 in which, when in use, the medical procedure is actually performed. To increase the size of the working cavity in comparison with prior art circular cross-section dissection tools, the main body 24 of preferred embodiments of the dissection tip 20 of the present invention includes a pair of lateral extensions 32, as best shown in FIGS. 3, 4 and 6. Each lateral extension 32 is formed from a lower, side portion of the hollow body 24 that is flared in an outward and upward direction with respect to the overall convex outer surface of the main body 24. As can be seen in FIGS. 3, 5 and 6, each lateral extension 32 extends beyond the nominal circumference of the main body 24 of the dissection tip and preferably beyond the cross-sectional profile of the cannula. In use, this increases the width of the working cavity formed in the tissue, since the lateral extensions 32 tend to direct the separated tissue layers away from the longitudinal axis of the main body 24 and cannula 22.

In the embodiments illustrated in the accompanying figure, the tip 20 of the dissecting device is separate from the cannula 22. The tip includes a connecting sleeve 34 that extends from the proximal end of the tip and is shaped in a complimentary fashion to the outside profile of the cannula 22 so as to receive the distal end of the cannula within the connecting sleeve. The connecting sleeve is preferably dimensioned relative to the cannula profile so as to allow the connecting sleeve to be securely fastened to the cannula, for example by gluing, welding, soldering, friction push fit or any other suitable fixing method. This allows the assembled dissection device to be withdrawn from an incision without the tip becoming disconnected from the cannula. This also allows the dissection tip and cannula to be separately sterilized or discarded as required. In alternative embodiments the tip 20 and cannula 22 may be integrally manufactured as a single element. It is envisaged that various dissection tip and cannula pairs may be encompassed in various embodiments of the present invention in accordance with the intended surgical use. For example, a longer cannula is likely to be required for the treatment of compartment syndrome than for the treatment of DeQuervain's syndrome.

As previously noted the cannula 22 is hollow. This allows at least an endoscope to be passed along the interior of the cannula to provide a view of either the working cavity formed by the dissection tip 20 or the immediate point of tissue dissection. In preferred embodiments one or more surgical instruments may also be passed through the cannula interior. In the preferred embodiment illustrated in the accompanying figures the internal and external cross-section of the hollow cannula 22 is substantially triangular, as shown in FIG. 7. The cannula 22 is arranged such that the endoscope passes along the uppermost central portion of the cannula 22, indicated by the dotted circle 36 shown in FIG. 7. The instruments are then able to pass through the remaining space below the endoscope, indicated by the dotted oval 38 in FIG. 7. The single oval space below the endoscope allows a range of instruments to be passed through the cannula into the working cavity formed by the dissector tip 20 and also allows the instruments to be freely moved within the cavity. However, it will be appreciated that alternative arrangements may be provided, such as two enclosed round channels or open space reflecting the outside profile of the cannula 22.

In embodiments in which a discrete passage for the endoscope is not provided within the cannula interior, guides are provided to maintain the endoscope in the upper central portion of the cannula. The guides are preferably located at both ends of the cannula, so as to minimise friction between the guides and the endoscope. A guide located at the proximal end of the cannula can be seen in FIG. 5. The guide 40 is the form of a planar plate having an outer profile matching the inner profile of the cannula and extending perpendicular across the interior of the cannula 22. The plate has one or more apertures formed therein that define the passageways through which the endoscope and instruments pass when the device is in use. In all embodiments of the present invention the cannula interior, including any provided guides, is arranged such that the endoscope lies along the axial plane of the cannula and the dissector tip 20. This is so that the central axis of the endoscope is always sufficiently below the tissue dissection portion 25 of the dissector tip. This is highly advantageous since it enables an uninterrupted view via the endoscope of the tissue structures immediately ahead of the dissection portion, thus allowing the operator to manipulate the device exactly as required to dissect the required tissue area. In prior art dissection devices in which the dissection tip does not lie above the axis of the endoscope this precise placement of the device is not possible, due to the impeded view via the endoscope.

There are two main modes, or configurations, in which the dissection device is intended to be used. When the dissection device is to be used to separate tissue layers, during which the dissection tip is pushed forward to physically separate the tissue layers, it is desirable for the tip of an endoscope, introduced via the cannula 22, to be as close to the dissection portion 25 as possible. This is substantially the configuration illustrated in FIGS. 3 and 5, in which an endoscope 42 is in close proximity to the dissection portion 25 of the dissector tip 20. To prevent the endoscope from being advanced to far forwards towards the dissection portion 25 and possibly being either damaged or being forced into content with the tissue being dissected, a stop 44 is located on the underside of the dissection tip 20 that is axially aligned with the endoscope and prevents it from being advanced too far. The stop 44 is a small projection against which an upper portion of the endoscope 42 can abut whilst not impeding the field of view of the endoscope to a significant extent. It will be noted that although the axis of the endoscope lies below the actual dissection portion 25 of the dissection tip 20, thus affording a clear view ahead as the device is advanced, the endoscope tip is wholly within the working cavity created by the dissection tip 20. In contrast however, on completion of the dissection it is then desirable to position the end of the endoscope 42 towards the rear of the working cavity 30, approximately level with the guide plate 40 shown in FIG. 5. In this position, illustrated in FIG. 8, the endoscope provides a clear view of the working cavity and of any instruments that have been introduced into the cavity via the hollow cannula 22, without impeding the use of such instruments in any way.

As previously mentioned, in preferred embodiments the desired surgical instruments are introduced into the working cavity 30 through the hollow interior. However, in alternative embodiments the lower surface of the cannula 22 may include an open slot 46, as shown in FIGS. 3, 5 and 8. The slot 46 provides guidance for a surgical instrument to be slid along the length of the cannula 22 along the outside of the cannula, the surgical instrument preferably being provided with appropriate means of engaging with the slot 46. The provision of a slot 46 in the underside of the cannula 22 allows a further instrument to be introduced to the working cavity in the event that insufficient space is available within the hollow cannula.

Although the use of the dissection device in the dissection mode does not require a significant force to be applied to the tip of the dissection device so as to separate the required layers of tissue, it is highly desirable to fully and easily control the movement of the dissector device tip to avoid damaging surrounding anatomical structures, such as adjacent nerves. To fulfil these requirements the dissector device is provided with an ergonomic handle 48, as shown in FIGS. 9 and 10. The handle is dimensioned to provide a comfortable single-handed grip by the surgeon. The handle 48 may be provided with appropriate shaped finger grips to provide a more comfortable grip to the user. An upper portion of the handle is angled away from an axis perpendicular to the longitudinal axis of the cannula 22 i.e. in use the handle is angled slightly towards the direction in which dissection is to be performed.

The lower portion of the handle 48 extends forward of the upper hand grip and includes a cannula receiving portion 50 that is arranged to receive the distal end of the hollow cannula 22. The cannula receiving portion 50 preferably includes a clamping mechanism, such as one or more hand operated screws, for securely fastening the cannula 22 to the handle 48. However, in alternative embodiments the cannula may be integrally bonded to the handle, for example by welding, gluing or soldering, or may be manufactured as a single element. Consequently, in certain embodiments the handle, cannula and dissection tip may form a single element.

The handle preferably includes a mechanism arranged to hold a commercially available endoscope and allow the endoscope to be moved back and forth within the cannula 22. An example of a suitable endoscope movement mechanism is schematically illustrated in FIGS. 11 and 12. The endoscope 42 is held by a connector piece 52 that in the embodiment illustrated is in the form of a 3-sided snap-fit 'saddle' having a thrust lug 54 protruding on either of the depending side pieces. The endoscope 42 is free to move back and forth by virtue of being supported by the hollow cannula 22 as previously discussed. An operating lever 55 is provided that is free to pivot about two opposing pivot points 56. The operating lever will be located within the handle 48 of the dissection device and is provided with an actuating portion 58, that in the embodiments shown is in the form of a closed loop 60 that protrudes from a corresponding aperture in the handle 48, as can be seen from FIGS. 9 and 10. The lower portion of the operating lever 55 includes a pair of thrust forks 62 arranged to movably fit on either side of the connector piece with the thrust lugs 54 located between the legs of each thrust fork 62. It will be appreciated that the mechanism described above is only one example of a suitable mechanism and other variants may be adopted without deviating from the scope of the present invention. For example, a single sided arrangement may be adopted that only utilises single sided pivots. Equally, an arrangement may be provided that utilises a series of gears rather than levers, or a combination of both.

In use a user will group the handle 48 with one hand, locating a finger in the closed loop 60 of the operating lever 55. To advance the endoscope 42 to the proximal end of the dissection tip 20 the operating lever 55 is pulled towards the user, causing the lever to pivot about the pivot points 56 and imparting a forward thrust onto the connector piece 52 via the thrust forks 62 and thrust lugs 54. FIG. 12 illustrates this position. To retract the endoscope the reverse operation is performed. A spring, or other suitable resilient member, may be provided to resiliently bias the endoscope 42 and operating lever 55 in either the extended or retracted positions. Additionally the mechanism for moving the endoscope back and forth may be arranged such that pulling the operating lever towards the user causes the endoscope to be retracted, although this less ergonomically desirable. The closed loop 60 is preferably provided to facilitate the user in lifting the whole dissection device as required. However, this function may equally be provided by including an alternative closed loop or other hook on the handle 48 itself.

As can be best seen in FIG. 10, the rear face of the handle 48 is open to allow a light cable 62 to be introduced and housed within the main body of the handle. The light cable 62 is arranged to be connected to the endoscope 42 to provide illumination to the endoscope tip in a manner known to those skilled in the art. In preferred embodiments one or more cable gripping elements are provided to hold the light cable securely within the handle. Additional or alternative means may be provided to close the rear face of the handle after the light cable 62 has been located within the handle. For example a pair of resilient lips may be provided that are spaced apart by a distance less than the width of the light cable, such that although the cable can be urged through the lips to either place it within the handle or remove it from the handle, it is unlikely to do so accidentally. In a further embodiment the handle 48 may be closed, in which case the light cable is threaded through a suitable aperture in the upper face 64 of the handle. A rubber grommet may be provided in the aperture to grip the light cable 62.

The handle 48 has a substantially flat underside 66, as shown in FIG. 13, such that when in use the cannula 22 can be placed as close to the skin of the patient as possible, allowing an entry into the body at a small angle. Within the underside 66 of the handle there is an approximately v-shaped recess 68 in communication with the open proximal end of the cannula 22, thus allowing surgical instruments 70 to be introduced into the cannula either from below or the sides of the cannula. This freedom of movement provided by the shaped recess 68 allows rotational, axial and lateral movements of the instruments within the cannula. The v-shaped recess preferably also allows an instrument to be introduced into the axial slot in the cannula 22, where such a slot is provided. The instruments to be used with the device may be any existing instruments, such as a pull-knife, push-knife, scissors or a probe. Alternatively the instruments may be custom made.

Whilst the embodiments of the current invention discussed herein make use of an endoscope and light cable, alternative embodiments may be provided in which either or both are substituted by integrated silicon chip devices. For example the endoscope may be replaced by a CCD imaging chip, in which case the chip is mounted at the distal end of a suitable shaft, that may have the necessary electrical wiring housed within it, that is mounted within the cannula and is movable back and forth in an analogous manner to that described above in relation to the endoscope. Alternatively, two separate CCD imaging chips may be utilised, one being mounted proximal to the dissection portion 25 of the dissection tip 20 and the other being mounted at the distal end of the cannula/dissection tip. Thus the proximally mounted imaging chip provides direct vision during advancement of the dissection device and tissue dissection, whilst the second chip provides direct vision of the working cavity. In this embodiment there is no longer any requirement for a mechanism to move an endoscope or equivalent shaft back and forth within the cannula to switch between direct vision of the tissue to be dissected and the working cavity.

In use a small incision is made in an area distant to the site of the required minimally invasive surgery and the dissector tip is inserted into the incision. At this point, the tip of the endoscope is in the forward, dissection mode, position such that the surgeon has, via the camera output, a direct view of the anatomical structure under dissection. By manipulating the handle 48 of the dissection device, the surgeon drives the dissection tip forward so as to separate the required layers of tissue. When the tip of the dissector has reached the desired anatomical structure, as determined from the direct view provided by the endoscope, forward motion of the dissector device is stopped and the endoscope tip is retracted to the surgery position. The working cavity 30 of the dissector is now positioned over the anatomical structure on which the minimally invasive surgery is to be conducted and enables the surgery to be conducted. The required surgical tools are then inserted through the cannula 22 via means of the v-shaped recess 68 provided in the under body of the handle 48 and are manipulated by the surgeon to complete the desired surgical procedure. Direct view of the working cavity and the surgical tools is provided by the endoscope in the retracted, surgery position. The tools and dissector may then be withdrawn and the single small incision closed. If necessary, the working cavity may be enlarged by the appropriate manipulation of the dissection tip 20 by means of appropriate manipulation of the handle 48 by the surgeon.

One example of the use of the dissector device according to embodiments of the present invention is in the treatment of DeQuervain's disease. Once called washerwoman's sprain, DeQuervain's is an extremely painful inflammation of the thumb side of the wrist and is one of the ailments generally commonly affecting women. Passing over the back of the wrist are the tendons for muscles that extend or straighten the fingers and thumb and lift the hand at the wrist. These tendons run through six lubricated tunnels (compartments) under a thick fibrous layer of tissue. One such compartment lies over the bony bump at the base of the thumb and two of the tendons that operate the thumb muscles pass through this compartment. The primary reason for pain with DeQuervain's is the constant friction of these tendons in the narrowed compartment. To reduce excess friction and thus alleviate the pain, traditional surgical techniques involved the opening of the compartment to surgically enlarge it and thus reduce the friction. However, when dissecting the tissue to get access to the extensor compartment a nerve branch can easily be damaged further. Possible complications include adherence of the tendons and nerves to the scar tissue that results from the open surgery and the relatively large visible scar generated as a result of the open surgery.

Treatment of DeQuervain's by minimally invasive surgery using the dissector device according to embodiments of the present invention substantially relieves or avoids many of the disadvantages and complications associated with the traditional or surgical treatment of DeQuervain's. Of particular advantage is the direct vision provided during both the dissection and surgical stages by the endoscope, which greatly reduces the accidental damage to nerves and tendons in the surrounding area.

A further example of a condition that may be treated by minimally invasive surgery using a dissector device according to embodiments of the present invention is that of compartment syndrome. Compartment syndrome occurs as a result of a trauma to a limb, typically the forearm or lower leg. The trauma may be in the form of a fractured or broken bone or deep bruising. The trauma tends to cause swelling of one or more of the underlying tissues. Since the swelling is not at the surface tissue layer, it is confined within the underlying layers of the limb and thus causes an increase in internal pressure. The increase in pressure often inhibits the arterial or venous blood flow to the surrounding tissue and this in turn can, if not treated, cause cell and tissue death within the limb, which may ultimately force the amputation of part of or all of the affected limb. The traditional treatment of compartment syndrome is to make a large incision through the skin and underlying tissue layers on either side of the limb to a depth necessary to reach the swollen tissue layer and thus relieve the internal pressure. The incision can, in some circumstances, extend along substantially the full length of the limb. However, this effectively creates an open wound that requires skin grafting, as well as resulting in later gross cosmetically unacceptable scarring, and also presents a potential site for infection.

To treat compartment syndrome using minimally invasive surgery, a small incision may be made and the dissector device according to embodiments of the present invention inserted and subsequently manipulated so as to cause dissection between the swollen tissue layer and the overlying tissue layer. A surgical knife may then be introduced through the cannula 22 to the working cavity. The knife is then used to create an internal incision in the swollen tissue layer along the desired length of tissue. This may be accomplished by either making the incision simultaneously as the dissector is advanced, by alternatively advancing the dissector and making a continuation of the incision or firstly advancing the dissector and then making the incision under direct vision (via the endoscope, for example) as the dissector is withdrawn. The internal incision is sufficient to relieve the tension within the swollen tissue layer and thus prevent the restriction of blood flow and prevent gross scarring.

A dissector device according to embodiments of the present invention may also be used for the harvesting of muscle flaps for reconstructive purposes. As an example, the latissimus dorsi muscle (LD) is harvested for several purposes, such as breast reconstruction or wound closure of large wounds. Previously, the LD was harvested in an open procedure leaving a scar of approximately 10 cm. However, endoscopic procedures have been introduced using standard endoscopic equipment. A dissector according to an embodiment of the present invention may be used to provide a more efficient and quicker alternative to the standard equipment.

A further use of the claimed dissector device is for mobilizing muscles for tendon transfer surgery in cerebral palsy and/or radial palsy and additionally for creating the subcutaneous "tunnels" for the muscles to-be-transferred to their new insertion. Tendon transfer surgery is sometimes indicated in patients with deformities of the extremities due to muscle spasticity or paralysis. The aim is to correct the imbalance of muscle forces around the affected joints by transposing muscles to opposite locations (e.g. transfer of the flexor carpi ulnaris to the extensor carpi radialis brevis muscle). For that the muscles must be dissected from their environment and re-located through subcutaneous tunnels. The advantage of the claimed dissector is that the dissection may be done leaving smaller scars. Attachment of the transposed muscle to the receptor tendon may even be done without opening of the skin at all at that side of the extremity.

The harvesting of veins or nerves may also be possible using the dissector of embodiments of the present invention. Currently described minimal invasive methods rely on two incisions: one for the dissector and camera; and one for the instruments. Since the dissector of the present application allows dissection and subsequent instrument procedures to be performed with the same device, the vein harvesting can be accomplished using the same single incision.

The invention claimed is:

1. A tissue dissection tip arranged to be attached to a distal end of an elongate cannula, the dissection tip comprising:
   a curved hollow shroud that when the dissection tip is orientated for use defines a substantially concave working cavity having an open underside, the hollow shroud comprising a pair of laterally extending lateral extensions, each lateral extension extending from an opposing lateral portion of a periphery of the hollow shroud and being positionally fixed with respect to the hollow shroud,
   wherein through a cross-section perpendicular to a longitudinal axis of the cannula, the hollow shroud has an outer surface having a substantially convex portion and each lateral extension has a substantially concave outer surface whereby the substantially outer concave surface of each lateral extension lifts upper dissected tissue, wherein the lateral extensions and the hollow shroud are formed together as a monolithic construction.

2. A tissue dissection tip according to claim 1, wherein the dissection tip comprises a tissue dissection portion located at a distal end of the dissection tip, the tissue dissection portion terminating in a plane that, when the dissection tip is orientated for use, is above a plane in which a remote viewing device is arranged to lie.

3. A tissue dissection tip according to claim 1, wherein through an axial cross-section the tissue dissection portion has a substantially concave outer surface that is contiguous with the convex outer surface of the hollow shroud.

4. A dissection device comprising:
   an elongate cannula having proximal and distal ends and a longitudinal axis,
   a handle arranged to be attached to the proximal end of the elongate cannula; and
   a tissue dissection tip according to claim 1.

5. A dissection device according to claim 4, wherein the cannula is further arranged to receive at least one surgical instrument therein.

6. A dissection device according to claim 4, wherein the cannula includes an elongate slot arranged to engage a surgical instrument and guide said instrument along said slot.

7. A dissection device according to claim 4, wherein the handle comprises a viewing device holding mechanism, said viewing device holding mechanism being arranged to translate a viewing device within the cannula between a first and second position.

8. A dissection device according to claim 7, wherein in the first position the distal end of a remote viewing device held by the viewing device holding mechanism extends beyond the distal end of the cannula and into the working cavity defined by the curved hollow shroud.

9. A dissection device according to claim 7, wherein the viewing device holding mechanism comprises an actuating lever arranged to be operated by a user whilst gripping the handle.

10. A dissection device according to claim 4, wherein a body portion of the handle is arranged to house a fiber optic cable for connection to the remote viewing device.

11. A dissection device according to claim 10, wherein the handle comprises a fiber optic cable retention mechanism arranged to secure a fiber optic cable within the handle.

12. A dissection device according to claim 11, wherein the fiber optic cable retention mechanism comprises a pair of resilient seals defining a slot arranged to receive the fiber optic cable there-through.

13. A dissection device according to claim 4, further comprising a remote viewing device, the remote viewing device comprising either an endoscope or a semiconductor imaging element.

14. A dissection device according to claim 4, further comprising a first semiconductor imaging element located at the proximal end of the dissection tip and arranged to provide a direct view immediately ahead of the dissection tip and a second semiconductor imaging element located at the distal end of the dissection tip and arranged to provide a direct view of the working cavity.

15. A dissection device according claim 4, wherein the handle includes a longitudinal groove in communication with the interior of the cannula.

16. A dissection device according to claim 15, wherein the longitudinal groove is in communication with an elongate slot in the cannula.

17. A dissection device according to claim 15, wherein the longitudinal groove is tapered in width towards the cannula.

18. A dissection device according to claim 4, wherein the handle comprises a grip portion arranged to provide a gripping area for a user's hand, the grip portion extending in a direction lateral to the axis of the cannula.

19. A dissection device according to claim 4, wherein the handle and the cannula are arranged to be separable from one another.

20. A dissector device according to claim 4, wherein the cannula comprises a plurality of internal longitudinal passageways.

21. A dissector device according to claim 20, wherein at least two of the internal longitudinal passageways are in communication with one another.

22. A tissue dissection tip arranged to be attached to a distal end of an elongate cannula, the dissection tip comprising:
   a curved hollow shroud comprising a body that when the dissection tip is orientated for use defines a substantially concave working cavity having an open underside, the hollow shroud comprising a pair of laterally extending lateral extensions, each lateral extension being formed from a side portion of the body,
   wherein through a cross-section perpendicular to a longitudinal axis of the cannula,
   the hollow shroud has an outer surface having a substantially convex portion and each lateral extension has a substantially concave outer surface whereby the substantially outer concave surface of each lateral extension lifts upper dissected tissue, wherein the lateral extensions and the hollow shroud are formed together as a monolithic construction.

23. A tissue dissection tip arranged to be attached to a distal end of an elongate cannula, the tissue dissection tip comprising:
   a tissue dissection portion located at a distal end of the dissection tip;
   a curved hollow shroud that when the dissection tip is orientated for use defines a substantially concave working cavity having an open underside, the hollow shroud comprising a pair of laterally extending lateral extensions, each lateral extension extending from an opposing lateral portion of a periphery of the hollow shroud and defining a lateral edge that extends from the tissue dissection portion,
wherein through a cross-section perpendicular to a longitudinal axis of the cannula, the hollow shroud has an outer surface having a substantially convex portion and each lateral extension has a substantially concave outer surface whereby the substantially outer concave surface of each lateral extension lifts upper dissected tissue, wherein the lateral extensions and the hollow shroud are formed together as a monolithic construction.

24. A tissue dissection tip according to claim 1, wherein the lateral extensions are arranged so as to be non-movable with respect to the hollow shroud.

* * * * *

UNITED STATES PATENT AND TRADEMARK OFFICE
CERTIFICATE OF CORRECTION

PATENT NO. : 8,721,527 B2  
APPLICATION NO. : 11/815970  
DATED : May 13, 2014  
INVENTOR(S) : Braam et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1701 days.

Signed and Sealed this
Twenty-ninth Day of September, 2015

Michelle K. Lee
*Director of the United States Patent and Trademark Office*